(12) United States Patent
Bymose et al.

(10) Patent No.: US 7,345,023 B2
(45) Date of Patent: Mar. 18, 2008

(54) TREATMENT OF HYPERPROLIFERATIVE CONDITIONS OF BODY SURFACES

(75) Inventors: Bjarne Bymose, Kgs. Lyngby (DK); Thomas Broe Christensen, Hinnerup (DK)

(73) Assignee: Valderm ApS, Kgs. Lyngby (DK)

( * ) Notice: Subject to any disclaimer, the term of this patent is extended or adjusted under 35 U.S.C. 154(b) by 216 days.

(21) Appl. No.: 10/486,648

(22) PCT Filed: Aug. 12, 2002

(86) PCT No.: PCT/DK02/00530

§ 371 (c)(1),
(2), (4) Date: Jul. 23, 2004

(87) PCT Pub. No.: WO03/015759

PCT Pub. Date: Feb. 27, 2003

(65) Prior Publication Data

US 2004/0242507 A1     Dec. 2, 2004

(30) Foreign Application Priority Data

Aug. 14, 2001    (DK) .......................... PA 2001 01218

(51) Int. Cl.
*A61K 31/70*    (2006.01)
(52) U.S. Cl. ......................... 514/34; 536/6.4
(58) Field of Classification Search ................ 536/6.4; 514/34

See application file for complete search history.

(56) References Cited

U.S. PATENT DOCUMENTS 4,946,683 A * 8/1990 Forssen ...................... 424/422
6,231,855 B1 * 5/2001 Ghione et al. ........... 424/130.1
6,555,095 B1 * 4/2003 Garrison ...................... 424/59

OTHER PUBLICATIONS

Onrust, et al., "Valrubicin", *Drugs & Aging*, vol. 15 (1), pp. 69-75, Jul. 1999.
Caplus Abstract 1991:415497 (1991) of Katada, T. "Effectiveness of doxorubicin hydrochloride (adriamycin) ointment on malignant skin lesions", Sei Marianna Ika Daikaku Zasshi, 18(5):818-31 (1990).
Dantchev, et al., "Comparative Microscopic Study of Cardiotoxicity And Skin Toxicity Of Anthracycline Analogs", *Biomedicine & Pharmacotherapy*, vol. 38, pp. 322-328, 1984.
Dantchev, et al., "Electron Microscopic Studies of the Heart and Light Microscopic Studies of the Skin After Treatment of Golden Hamsters With Adriamycin, Detorubicin, AD-32, and Aclacinomycin", *Cancer Treatment Reports*, vol. 63, pp. 875-888, May 1979.
Dantchev, et al., "Ultrastructural Study of the Cardiotoxicity and Light-Microscopic Findings of the Skin After Treatment of Golden Hamsters with Seven Different Anthracyclines", *Recent Results Cancer Res.*, vol. 74, pp. 223-249, 1980.
Sweatman, et al., "Pharmacologic rationale for intravesical N-Trifluoroacetyladriamycin-14-valerate (AD 32): a preclinical study", *Cancer Chemother Pharmacol.*, vol. 28, pp. 1-6, 1991.
Anthra Pharmaceuticals, Inc., "Valstar™ (valrubicin) Sterile Solution for Intravesical Instillation", FDA NDA 20,892, pp. 1-11, 2001.

* cited by examiner

*Primary Examiner*—Elli Peselev
(74) *Attorney, Agent, or Firm*—Iver P. Cooper (57) ABSTRACT

The present invention relates to pharmaceutical formulations comprising an anthracycline and the uses thereof for treatment of clinical conditions of body surfaces such as skin and mucosal membranes, wherein abnormal cell differentiation and/or hyperproliferation is a primary factor of the pathogenesis. In particular the invention relates to treatment of psoriasis, and preferably to treatment of psoriasis with valrubicin topically applied.

14 Claims, 2 Drawing Sheets

TREATMENT OF HYPERPROLIFERATIVE CONDITIONS OF BODY SURFACES

FIELD OF THE INVENTION

The present invention relates to pharmaceutical formulations comprising an anthracycline and the uses thereof for treatment of clinical conditions of body surfaces such as skin and mucosal membranes, wherein abnormal cell differentiation and/or hyperproliferation is a primary factor of the pathogenesis.

BACKGROUND OF THE INVENTION

Anthracyclines

Anthracyclines are antibiotics having potent antineoplastic activity, and accordingly they have been used in the treatment of a variety of cancers. The cytostatic effect of most anthracyclines is achieved by affecting DNA functions for example inhibition of RNA synthesis usually by intercalating with DNA.

The group of anthracyclines for example comprises doxorubicin, valrubicin, epirubicin, daunorubicin and idarubicin. Doxorubicin and epirubicin have been applied against a broad spectrum of neoplastic diseases, whereas daunorubicin has primarily been applied against acute leukemia. Doxorubicin, daunorubicin, idarubicin and epirubicin are usually administered systemically by injection. Systemic administration of these anthracyclines however results in a number of undesirable side effects such as cardiotoxicity and bone marrow suppression.

Anthracyclines are in general known to be very tissue toxic. For example, paravenous injection of epirubicin results in severe necrosis and immediate measures have to be undertaken to avoid severe local toxicity.

Valrubicin is a semisynthetic analogue of doxorubicin and it is developed for the treatment of superficial bladder cancer and approved for such use in the United States. Usually a total of 800 mg is administered by 40 mg/ml intravesical instillation of two hours duration for a total of 6 times once a week. Such a treatment does not result in systemic uptake, but valrubicin may be found in an effective concentration 1800 μm into the epithelium of the bladder (7).

Psoriasis

Psoriasis is characterised by epidermal hyperproliferation including a highly increased growth of keratinocytes. Furthermore, parakeratosis, i.e. cell nuclei retained in stratum corneum may always be observed in psoriatic patients. With increased cell proliferation, there is an increased DNA synthesis in the affected tissue which has been the basis for assays for evaluation of the efficacy of anti-psoriasis agents.

Treatment of psoriasis depends on the kind of psoriasis and the degree of severity of the psoriasis to be treated. Psoriasis vulgaris, guttate psoriasis, flexural psoriasis, erythrodermic psoriasis, generalised pustular psoriasis and localised pustular psoriasis are the most common forms of the disease.

Commonly used treatments against psoriasis may for example be

Local treatment with vitamin-D derivative ointments or creams. Vitamin D is slow working and can cause temporary skin irritation.

Local treatment with steroid ointments that may inhibit inflammation associated with psoriasis. Common side effects of steroids include thinning of the skin, easy bruising and stretch marks. Furthermore, administration of steroids often results in rebound phenomena.

Coal tar ointment or coal tar baths that may inhibit inflammatory processes in the skin. Coal tar may make the skin more sensitive to ultraviolet light and tar products stain clothing and linens, and may be irritating to the skin.

Potassium-permanganate baths that have a disinfecting effect.

Climatotherapy, for example sunbathing and bathing in saltwater for example at the Dead Sea. However 10% of psoriatic patients are hypersensitive against sunlight and sunburn can cause psoriasis to get worse. Furthermore, sunbathing increases the risk of skin cancer.

These treatments are frequently not effective and especially more severe cases of psoriasis cannot be treated using the above mentioned treatments. More severe cases of psoriasis may instead be treated with light therapy which, however, must be performed at the hospital or clinic. Light therapy can for example be:

Ultraviolet light treatment (UVB), which especially is applied in cases where the psoriasis is widespread, but not very thick, because UVB can not penetrate a thick layer.

Ultraviolet light and tablet treatment (PUVA) that is a combined treatment involving administration of 8-methoxypsoralen that increases the sensitivity of the skin towards UVA therapy and therapy with UVA. The side effects of this treatment involve nausea and in certain cases increased biochemical liver values. Moreover UVA irradiation results in an increased risk of skin cancer and premature ageing of the skin Very severe cases of psoriasis that may not be effectively treated with either of the above mentioned treatments may be treated with a systemic treatment agent such as for example:

Methotrexate—a cytostatic, which is also used in the treatment of cancer. The dose is lower than what is used in cancer treatment. Short-term side effects of methotrexate include nausea, fatigue, loss of appetite and mouth sores, whereas long-time side effects may include damages to the liver.

Sandimmun/cyclosporin—an immune inhibiting compound that is also used in organ transplantation that inhibits the abnormal immune processes in the skin of psoriatic patients. Side effects may be severe. They are similar to the side effects caused by other cytotoxic agents and include myelosuppression, decreased resistance to infections and risk of secondary neoplasms.

Acitretin—a vitamin A like compound that inhibits inflammation. Acitretin is only effective against pustular and erythrodermic types of psoriasis, and increases the risk of causing birth defects in developing fetuses.

The side effects of these treatments are considerable and hence it is not desirable to use any of these treatments to frequently.

SUMMARY OF THE INVENTION

Accordingly, there is a great need for new improved treatments against psoriasis that are effective, but do not cause adverse side effects.

Cytostatic compounds such as methotrexate used to treat psoriasis must be administered systemically in order to be effective. Systemic administration results in an increased risk of side effects, some of which may be severe. No effective cytostatic compound is currently available that may be applied topically to the site of disease without causing local toxicity to the skin.

The present invention discloses that a number of cytostatic compounds, namely members of the group of anthracyclines as well as derivatives thereof, may be used in topical formulations for the treatment of psoriasis and other clinical conditions of body surfaces, wherein hyperproliferation is a primary factor of the pathogenesis.

Hence it is a first objective of the present invention to provide pharmaceutical compositions comprising an anthracycline and/or a derivative thereof together with one or more pharmaceutically acceptable carriers, wherein said pharmaceutical condition is formulated for topical administration to a body surface.

It is a second objective of the present invention to provide methods of treatment of a condition associated with hyperproliferation or pre-neoplastic or neoplastic processes of a body surface in an individual in need thereof comprising administering a pharmaceutical composition comprising an anthracycline topically to said individual.

It is a third objective of the present invention to provide uses of pharmaceutical composition comprising an anthracycline for the preparation of a medicament for the treatment of a condition associated with hyperproliferation or pre-neoplastic or neoplastic processes of a body surface.

DETAILED DESCRIPTION OF THE INVENTION

Anthracycline

Anthracyclines according to the present invention are a class of antibiotics that are derived from an actinomycete of the genus *Streptomyces* as well as derivatives thereof. As anthracyclines are capable of inhibiting DNA and/or RNA synthesis they are useful as antineoplastic agents and the group currently comprises more than 500 species. Any anthracycline may be used with the present invention.

For example anthracyclines and/or derivatives thereof may be selected from the group consisting of doxorubicin, valrubicin, epirubicin, daunorubicin, idarubicin, aclarubicin and 5-iminodaunorubicin-dexrazoxane, pirarubicin, zorurubicin, amrubicin hydrochloride, N-acetyladriamycin and derivatives thereof.

In one embodiment of the present invention the anthracycline is selected from the group of anthracyclines with the general formula wherein $R_1$ and $R_2$ may individually be selected from the group consisting of —H, acyclic alkyls, cyclic alkyls, aryls, heteroaryls, alkenyls, alkynyls, alkoxyls, amines, hydroxyls, carboxyls, carboalkoxyls, esters, aryl esters, alkoxyl esters, amids, aryl amids, heterocycles and any of the aforementioned substituted with one or more of hydroxyl, bromo, fluoro, chloro, iodo, mercapto, thio, cyano, alkylthio, heterocycle, aryl, heteroaryl, carboxyl, carboalkoyl, alkyl, alkenyl, nitro, amino, alkoxyl and/or amido.

For example $R_1$ and $R_2$ may individually be selected from the group consisting of —$NH_2$, $C_{1-10}$ alkoxyl, $C_{1-10}$ alkoxyl ester and $C_{1-10}$ alkoxyl substituted with hydroxyl and/or amine and/or fluoro.

In one preferred embodiment, $R_1$ and $R_2$ are individually selected from the group consisting of:
—$COCH_2OCO(CH2)_3CH_3$
—$COCH_2OH$
—$COCH_3$
—$NH_2$
—H
—OH
—$NHCOCF_3$ In one particularly preferred embodiment, $R_1$ is —$COCH_2OCO(CH2)_3CH_3$ and $R_2$ is —$NHCOCF_3$ Preferably, anthracyclines according to the present invention can inhibit and/or reduce proliferation of cells, such as for example proliferation of mammalian cells. This effect is preferably achieved due to one or more of the following:
  inhibition and/or reduction of DNA synthesis
  inhibition and/or reduction of RNA synthesis
  DNA Topoisomerase II inhibition
  inhibition of nucleoside transport Preferred anthracyclines according to the present invention are lipophilic anthracyclines. In particular, lipophilic anthracyclines are capable of passing the cell membrane easily and may enter the cytoplasm and nucleus of cells in a fast manner.

One example of a lipophilic anthracycline is valrubicin, which is very lipophilic due to the less ionisation compared to other anthracyclines. Accordingly, valrubicin may pass the cell membrane easily and may enter the cytoplasm of cells in a fast manner. Like other anthracyclines, valrubicin inhibits RNA and DNA synthesis.

Furthermore, preferred anthracyclines according to the present invention are capable of penetrating into a multilayered epithelium, preferably more than one cell layer, such as approximately 2 cell layers, for example approximately 3 cell layers, such as approximately 4 cell layers, for example approximately 4 to 6 cell layers, such as approximately 6 to 8 cell layers, for example approximately 8 to 10 cell layers, such as approximately 10 to 12 cell layers, for example approximately 12 to 15 cell layers into a multilayered epithelium. Especially it is preferred that the anthracycline according to the present invention when applied to human skin surfaces can penetrate into skin epithelium, more preferably, the anthracycline can penetrate 0.1 to 0.2 mm, such as 0.2 to 0.3 mm, for example 0.3 to 0.5 mm, such as 0.5 to 0.75 mm, for example 0.75 to 1.0 mm, such as 1.0 to 1.5 mm, for example 1.5 to 2.0 mm, such as 2.0 to 2.5 mm, for example 2.5 to 3.0 mm, such as 3.0 to 3.5 mm, for example 3.5 to 4.0 mm, such as 4.0 to 4.5 mm, for example 4.5 to 5.0 mm into the skin.

In addition, preferred anthracyclines according to the present invention are systemically absorbed in a limited manner after topically administration to a body surface.

Preferably, systemic absorption is less than 10%, such as less than 8%, for example less than 6%, such as less than 5%, for example less than 4%, such as less than 3%, for example less than 2%, such as less than 1%.

Systemic absorption may be determined by any conventional method, for example systemic absorption may be determined by measuring the amount of anthracycline in a blood sample or in serum. Anthracycline in blood and/or serum may for example be determined by HPLC.

Additionally, preferred anthracyclines according to the present invention are not locally toxic, when applied topically to a body surface of an individual, more preferably, the anthracyclines are not or are only mildly irritant when applied to a body surface of an individual in an effective dose (see herein below).

Histopathological animal experiments have shown that valrubicin does not affect normal dermal epithelium (1-3) and that application of vairubicin to skin and eyes in a concentration similar to the concentration of valrubicin used in the treatment of bladder cancer only results in mild to no irritation (4). Furthermore, valrubicin is less cardiotoxic and haematologically toxic than other anthracyclines (5;6).

Accordingly, in one preferred embodiment of the present invention the anthracycline is valrubicin or a derivative thereof. Valrubicin, also known as AD-32 or N-trifluoro-acetyladriamycin-14-valerate, is a semisynthetic derivative of doxorubicin. In table 1 properties of valrubicin and doxorubicin are listed.

TABLE 1

Pharmacodynamic and-kinetic properties of Valrubicin and Doxorubicin

|  | Valrubicin | Doxorubicin |
|---|---|---|
| Mechanisms | | |
| DNA binding | – | +++ |
| DNA Topoisomerase II inhibition | – (parent)<br>++ (metabolite) | ++ |
| DNA Synthesis inhibition | +++ (rapid) | +++ (slow) |
| RNA Synthesis inhibition | +++ (rapid) | + (slow) |
| Nucleoside Transport Inhibition | +++ | + |
| Pharmacology | | |
| Cellular Uptake  rate | Rapid | Slow |
| localisation | Cytoplasm | Nucleus |
| In vivo metabolism | Extensive | Minimal |
| In vivo elimination | rapid | Slow |

Body Surface

A body surface according to the present invention is any surface of an individual, which is easily accessible from the exterior of the individual. The body surface preferably comprises an epithelium or consists of an epithelium, which may comprise a monolayer of cells or may be multilayered. However, the body surface preferably does not comprise transitional epithelium.

For example the body surface may be selected from the group consisting of skin, mucosal membranes of the oral cavity, nose, vagina, eye, larynx, genital tract, lungs, bronchia, gastrointestinal tract and rectum. Preferably, the body surface is selected from the group consisting of skin, mucosal membranes of the oral cavity, nose, eye and vagina.

In one preferred embodiment the body surface is a mucosal membrane, preferably the mucosal membrane of the oral cavity.

In an especially preferred embodiment of the present invention, the body surface is the skin. Skin according to the present invention is composed of epidermis and dermis. The epidermis usually comprises 5 layers, which from inside to outside is stratum basale, stratum spinosum, stratum granulosum, stratum lucidum and strata corneum, wherein the stratum corneum consists of keratinised cells. Each of these layers may comprise one or more cell layers. The dermis underlies the epidermis and is a dense irregular connective tissue. The dermis may furthermore for example comprise hair follicles, sweat glands and/or nerve endings. The term "skin" within the meaning of the present invention may comprise one or more or all of the above mentioned layers and structures.

Conditions

The conditions to be treated according to the present invention are any condition of a body surface associated with hyperproliferation and/or pre-neoplastic and/or neoplastic processes. Preferably, the condition is a condition, wherein hyperproliferation is a primary factor of pathogenesis. More preferably, the clinical condition is associated with hyperproliferation of skin and/or mucosal membranes.

In one preferred embodiment of the present invention, the condition is associated with dermal hyperproliferation and/or dermal pre-neoplastic and/or neoplastic processes. Dermal hyperproliferation may for example be hyperproliferation of epidermis or hyperproliferation of dermis. However, preferably dermal hyperproliferation is hyperproliferation of the epidermis. Hyperproliferation of epidermis may for example involve hyperproliferation of stratum basale.

However, the condition according to the present invention may also be associated with hyperproliferation or pre-neoplastic or neoplastic processes of other body surfaces. Hence, a large number of different conditions may be treated according to the present invention. For example the condition according to the present invention may be selected from the group consisting of psoriasis, actinic keratosis, seborrheic keratosis, photo-induced keratosis, lichen planus, basocellular carcinoma of the skin, planocellular carcinoma of the skin, leucoplakia, erythroplakia, carcinoma in situ in the mouth, verruca vulgaris, condyloma acuminata of skin or mucosal membranes, cutaneous T-cell lymphomas, cutaneous metastasis and cicatricial hypertrophy.

In one embodiment the condition is cutaneous metastasis. The primary tumour from which the metastasis is derived may be any tumour; for example the primary tumour may be breast cancer.

In one preferred embodiment the condition is psoriasis. The term psoriasis according to the present invention includes all types of psoriasis known to the person skilled in the art. For example psoriasis may be selected from the group consisting of psoriasis vulgaris, guttate psoriasis, flexural psoriasis, erythrodermic psoriasis, generalised pustular psoriasis and localised pustular psoriasis. The psoriasis to be treated according to the present invention may be mild, moderate, more severe or very severe psoriasis, such as psoriasis wherein less than 2 percent, for example 2% to 5%, such as 5% to 10%, for example 10% to 15%, such as more than 15% of the skin is affected.

Administration Forms

The individual to be treated according to the present invention is preferably an individual suffering from a condition of a body surface associated with hyperproliferation and/or pre-neoplastic and/or neoplastic processes, preferably one of the above mentioned conditions. The individual may be any animal, however, preferably the individual is a human being.

The treatment may be ameliorating treatment and/or the treatment may be curative treatment and/or the treatment may be prophylactic treatment. In some embodiments of the present invention, the treatment may abolish or relieve some or all of the symptoms of the condition during treatment and/or for a specific period of time after cessation of-treatment, but then one or more symptoms may reappear. For example, the symptoms may reappear about 1 day, such as about 2 days, for example about 3 days, such as about 3 to 5 days, for example about 5 to 7 days, such as about 7 to 10 days, for example about 10 to 15 days, such as about 15 to 20 days, for example about 20 to 30 days, such as about 30 to 60 days, for example about 60 to 120 days, such as more than 120 days after cessation of treatment.

The pharmaceutical formulations according to the present invention are preferably administered topically.

Topical administration according to the present invention should be understood as local administration directly to the site of disease. Preferably, topical administration results in that the majority of the active compound i.e. anthracycline is not systemically absorbed and hence substantially only capable of exerting its effect locally at the site of application. Preferably, systemic absorption is less than 10%, such as less than 8%, for example less than 6%, such as less than 5% for example less than 4%, such as less than 3%, for example less than 2%, such as less than 1%.

The treatment may be administered once; however, the treatment is usually administered more than once, such as more than 2 times, for example more than 5 times, such as more than 10, for example more than 15, such as more than 20, for example more than 30 times, such as more than 50 times, for example more than 100 times, such as every time treatment is required.

When the treatment is administered more than once, the individual administrations may be distributed over a period of for example 1-2 hours, such as 2-5 hours, for example 5-10 hours, such as 10-24 hours, for example 1-2 days, such as 2-5 days, for example 5-10 days, such as 10-20 days, for example 20-30 days, for example 1-2 months, such as 2-5 months for example more than 5 months. In one preferred embodiment of the present invention, the individual administrations are distributed over a period of from 1 to 7 days, more preferably from 2 to 6 days, even more preferably from 3 to 5 days, most preferably around 4 days.

Furthermore, the time gap between two individual administrations may be less than 1 hour, or for example 1-2 hours, such as 2-5 hours, for example 5-10 hours, such as 10-24 hours, for example 1-2 days, such as 2-5 days, for example 5-10 days, such as 10-20 days, for example 20-30 days, for example more than 1 month. The time gap between two individual administrations may always be the same or it may different from time to time.

In one particular embodiment, treatment may be repeated at every occurrence and/or reoccurrence of the condition. At every occurrence and/or reoccurrence of the condition, a treatment regimen may be administered. Such a treatment regimen may comprise administration of the pharmaceutical composition once or more than once, such as more than 2 times, for example 2 to 5 times, such as 5 to 10, for example 10 to 15, such as 15 to 20, for example 20 to 30 times, such as more than 30 times per treatment regimen.

Each treatment regimen may be administered over a period of for example 1-2 hours, such as 2-5 hours, for example 5-10 hours, such as 10-24 hours, for example 1-2 days, such as 2-5 days, for example 5-10 days, such as 10-20 days, for example 20-30 days, for example 1-2 months, such as 2-5 months, for example more than 5 months.

The time gap between two individual administrations of a treatment regimen may be less than 1 hour, or for example 1-2 hours, such as 2-5 hours, for example 5-10 hours, such as 10-24 hours, for example 1-2 days, such as 2-5 days, for example 5-10 days, such as 10-20 days, for example 20-30 days, for example more than 1 month. The time gap between two individual administrations of a treatment regimen may always be the same or it may different from time to time.

The dose to be administered depends on the particular individual and condition and severity of condition to be treated as well as the mode of administration. In general, however, between 1 µg and 5 mg of anthracycline is administered.

In one embodiment, the anthracycline is administered in a dose of preferably 1 µg to 250 µg, more preferably 5 µg to 150 µg, even more preferably 10 µg to 100 µg, yet more preferably 15 µg to 75 µg, even more preferably 20 µg to 50 µg, yet more preferably 25 µg to 40 µg, even more preferably 25 µg to 35 µg, most preferably around 30 µg of anthracycline per dose. Such administration doses are for example suitable for administration in an occlusion bandage or for other administration forms.

In another embodiment, the anthracycline is administered in a pharmaceutical formulation that comprises from 0.01% to 10%, such as from 0.05% to 8%, for example from 0.1% to 7%, such as from 0.25% to 6%, for example from 0.5% to 5%, such as from 0.6% to 4%, for example from 0.7% to 2%, such as from 0.75% to 1.5%, for example from 0.8% to 1.2% w/w anthracycline. Furthermore, the anthracycline may be administered in a pharmaceutical formulation that comprises from 0.01% to 0.05%, such as from 0.05% to 0.1%, for example from 0.1% to 0.25%, such as from 0.25% to 0.5%, for example from 0.5% to 0.75%, such as from 0.75% to 1.0%, for example from 1,0% to 1.25%, such as from 1.25% to 1.5%, for example from 1.5% to 2.0% w/w anthracycline. Such administration doses are for example suitable when the anthracycline is administered formulated as a solution, gel, ointment, creme, lotion or in any other form suitable for topical administration.

In one embodiment the anthracycline is administered in an ointment that comprises around 1% or such as around 0.7% or for example around 0.5% w/w anthracycline.

Preferably, administration of the pharmaceutical compositions according to the present invention does not result in any severe malaise or any severe irritation, more preferably administration does not result in any significant nuisance to the individual to be treated, most preferably, administration does result in only mild and/or no malaise, irritation and/or nuisance.

Pharmaceutical Compositions

The pharmaceutical compositions according to the present invention preferably comprise at least one anthracycline together with one or more suitable pharmaceutically acceptable carriers. The pharmaceutical compositions according to the present invention are preferably formulated in a manner suitable for topical administration to a body surface.

The pharmaceutical composition according to the present invention may comprise more than one different anthracycline, such as 2, for example 3, such as 4, for example 5, such as more than 5 different anthracyclines.

The pharmaceutical composition may be formulated in a number of different ways dependent on the condition to be treated, the individual to be treated and the site of disease. Accordingly, the pharmaceutical composition is preferably formulated according to the need of the specific embodiment of the present invention.

For example the pharmaceutical composition may be selected from the group consisting of a suspension, solution, ointment, lotion, sexual lubricant, cream, foam, aerosol, spray, suppository, implant, inhalant, dry powder, syrup, balm and lozenge. Preferably however, the pharmaceutical composition may be selected from the group consisting of a lotion, an ointment, a gel, a cream, a transdermal patch, an occlusion bandage comprising a solution and/or suspension comprising the anthracycline and a spray.

In one preferred embodiment the pharmaceutical composition is formulated as a solution, ointment, lotion, cream or a gel. In particular, when the condition is psoriasis or another condition of the skin, it is preferred that the pharmaceutical composition is formulated as an ointment, lotion, cream or gel.

Pharmaceutical compositions containing an anthracycline according to the present invention may be prepared by conventional techniques, e.g. as described in Remington: The Science and Practice of Pharmacy 1995, edited by E. W. Martin, Mack Publishing Company, 19$^{th}$ edition, Easton, Pa.

Pharmaceutically acceptable salts of the compounds according to the present invention should also be considered to fall within the scope of the present invention. Pharmaceutically acceptable salts are prepared in a standard manner. If the parent compound is a base, it is treated with an excess of an organic or inorganic acid in a suitable solvent. If the parent compound is an acid, it is treated with an inorganic or organic base in a suitable solvent.

The compounds of the invention may be administered in the form of an alkali metal or earth alkali metal salt thereof, concurrently, simultaneously, or together with a pharmaceutically acceptable carrier or diluent.

Solutions, creams, ointments or gels according to the present invention are semi-solid formulations of the active ingredient for external application. They may be made by mixing the active ingredient in finely divided or powdered form, alone or in solution or suspension in an aqueous or non-aqueous fluid, with the aid of suitable machinery, with a greasy or non-greasy base, such as known to the person skilled in the art.

Examples of bases are bases that may comprise one or more hydrocarbons such as hard, soft or liquid paraffin, glycerol, paraffin oil, beeswax, a metallic soap; a mucilage; an oil of natural origin such as almond, corn, arachis, castor or olive oil or derivatives thereof such as castor oil polyoxyl; wool fat or its derivatives or a fatty acid and/or ester such as steric or oleic acid, or isopropyl myristate.

The base may furthermore comprise an alcohol such as propylene glycol, polyethylene glycol (PEG) of different molecular weights, cetyl alcohol, ethanol or a macrogel. The formulation may incorporate any suitable surface active agent or emulsifier such as an anionic, cationic or non-ionic surfactant such as a sorbitan ester, polysorbate, Cremophor EL, Tween 20, or a polyoxyethylene derivative thereof. Suspending agents such as natural gums, cellulose derivatives or inorganic materials such as silicaceous silicas, and other ingredients such as lanolin, may also be included.

Lotions according to the present invention include those suitable for application to the skin or eye. An eye lotion may comprise a sterile aqueous solution optionally containing a bactericide and may be prepared by standard methods. Lotions or liniments for application to the skin may also include an agent to hasten drying and to cool the skin, such as an alcohol or acetone, and/or a moisturiser such as glycerol or an oil such as castor oil or arachis oil.

In one preferred embodiment, the pharmaceutical formulations according to the present invention comprise one or more compounds selected from the group consisting of emulsifiers, hydroxy compounds and lipids. For example 2 compounds, such as 3 compounds, for example more than 3 compounds.

The emulsifier may be any emulsifier known to the person skilled in the art that is suitable for pharmaceutical formulations for topical administration. Preferably, the emulsifier is selected from the group consisting of Cremophor EL, Tween 20, polysorbate 80 and mixtures thereof, more preferably, the emulsifier is polysorbate 80. However, it is also contained within the present invention that the pharmaceutical composition comprises more than one emulsifier.

The hydroxy compound may be any hydroxy compound known to the person skilled in the art that is suitable for pharmaceutical formulations for topical administration. The pharmaceutical formulation may comprise more than one different hydroxy compound, such as 2, for example 3, such as 4, for example 5, such as 6, for example more than 6. Preferably, the hydroxy compound is selected from the group consisting of ethanol, glycerol, propylene glycol, polyethylene glycol (PEG), cetyl alcohol and mixtures thereof. PEG-may be any molecular weight PEG, preferably however PEG 6000. More preferably, the hydroxy compound is selected from the group consisting of ethanol, glycerol, propylene glycol, PEG 6000 and cetyl alcohol.

The lipid may be any lipid known to the person skilled in the art that is suitable for pharmaceutical formulations for topical administration. The term lipid as used herein comprises fatty acids and esters thereof. Preferably, the lipid is selected from the group consisting of fatty alcohols, fatty acid esters, mineral oil, oil of natural origin and derivatives thereof and mixtures thereof. More preferably the lipid is selected from the group consisting of Castor oil polyoxyl, paraffin oil and isopropyl myristate. The pharmaceutical composition according to the present invention may comprise only one kind of lipid or it may comprise more than one kind, such as 2, for example 3, such as more than 3 different lipids.

Examples of specific formulations according to the present invention are given in the examples herein below.

Combination Therapy

The pharmaceutical compositions according to the present invention may comprise one or more different active components in addition to the anthracycline, such as one, for example 2, such as 3, for example 4, such as 5, for example more than 5 different active components.

In one preferred embodiment the pharmaceutical composition furthermore comprises a second active component.

The second active component may be any active component known to the person skilled in the art. In a particularly preferred embodiment, the second active component is selected from the group of active components, which are known to be active against the condition to be treated.

Accordingly, when the condition is psoriasis, the second active component may be a component which is known in the art to be effective against psoriasis. For example the second active component may be selected from the group consisting of steroids, coal tar, calcipotriene, vitamin A, antralin and salicylic acid.

The methods of treatment disclosed by the present invention may also be combined with one or more second treatments. In one embodiment of the present invention, the second treatment may be treatment with a different anthracycline, so that the method comprises treatment with 2, for example 3, such as 4, for example 5, such as more than 5 different anthracyclines.

However, the second treatment according to the present invention may also be treatment which is not administration of an anthracycline. Preferably, the second treatment(s) may be selected from the group of treatments, which are known to be active against the condition to be treated.

Accordingly, when the condition is psoriasis the second treatment may be a treatment, which is known in the art to be effective against psoriasis. For example the second treatment may be selected from the group consisting of treatment with sunlight, ultraviolet light B (UVB) or PUVA. In particular, the anthracycline according to the present invention may sensitise the individual towards treatment with sunlight, ultraviolet light B (UVB) or PUVA, in a manner such as lower amount of light and/or irradiation is required to obtain the desired effect. Furthermore, the second treatment may be administration of at least one compound selected from the group consisting of steroids, coal tar, calcipotriene, vitamin A, anthralin, salicylic acid, methotrexate, retinoids and cyclosporin.

The anthracycline and the second treatment may be administered simultaneously or sequentially in any order. In one embodiment, the treatments are administered in a rotational manner, such as one treatment is administered for a specific predetermined amount of time, after which the second treatment is administered for a specific predetermined amount of time, after which the first treatment is administered again and so forth. Rotational treatment may also comprise more than 2, such as 3, for example 4, such as 5, for example more than 5 different treatments.

Each of the different treatments may be given once or more than once as described for the anthracyclines herein above.

When the condition is a neoplastic and/or preneoplastic condition, such as for example a cutaneous metastasis the second treatment may be any treatment known in the art to be effective against neoplastic and/or preneoplastic conditions.

For example the second treatment may be chemotherapy, including systemic or topical administration of any suitable cytostatica known to the skilled person. Furthermore the second treatment may be selected from the group consisting of surgical treatment, radiation therapy, therapy with cytokines, hormone therapy, gene therapy, dendritic cell therapy and treatments using laser light.

In one embodiment, the second therapy is preferably radiation therapy, more preferably radiation therapy comprising electron and/or photon irradiation. In particular, topical administration of anthracycline may sensitise locally against irradiation, so that radiation therapy may become more efficient.

EXAMPLES

The examples given herein are illustrative examples of embodiments of the present invention and should not be regarded as limiting for the invention.

Example 1

Pharmaceutical solution for topical administration comprising Valrubicin.

ValDerm Solution
A composition of the following ingredients:

|  | % |
|---|---|
| Valrubicin | 1 |
| Castor oil polyoxyl Ph.Eur. | 10 |
| Ethanol anhyd. | 39 |
| Glycerol anhyd. | 50 |
| Total | 100 | was prepared by dissolving Valrubicin in the mixture of Castor oil polyoxyl Ph. Eur. and Ethanol anhyd. Thereafter Glycerol anhyd. is added.

The following solution was prepared as described above.

| ValDerm (0.267 mg/g) | |
|---|---|
| Valrubicin 40 mg/ml | 0.5 ml |
| Cremophor El | 8.6 ml |
| Ethanol | 11.4 ml |
| Glycerol anhyd. | 55 ml |
| Placebo | |
| Cremophor El | 8.6 ml |
| Ethanol | 11.4 ml |
| Glycerol anhyd. | 55 ml |

Example 2

Treatment of Psoriasis Vulgaris

Either 5 drops of placebo (see example 1) or 5 drops of ValDerm (see example 1) were placed on waterproof occlusion bandages (OpSite', Post-Op, Smith+Nephew, 6.5 cm×5 cm). Subsequently, the occlusion bandages were placed on the left elbow (ValDerm) and the right elbow (placebo) on a patient suffering from psoriasis vulgaris, said patient having large, visible psoriatic plaques at both elbows at the time when treatment was initiated.

The occlusion bandages were renewed daily. When bandages were renewed, remains of old administered substance was removed and toxicology was estimated, before placing a fresh occlusion bandage with fresh ValDerm or Placebo. The condition of the elbows and knee was documented by digital photography (Kodak DC 265, 1,2 megapixel) with automatic time stamp on all pictures. Pictures were reduced to 12×8 cm and printed on a HP deskjet 970Cxi printer on premium glossy photo paper.

The treatment was administered for 4 days.

Figure 1:
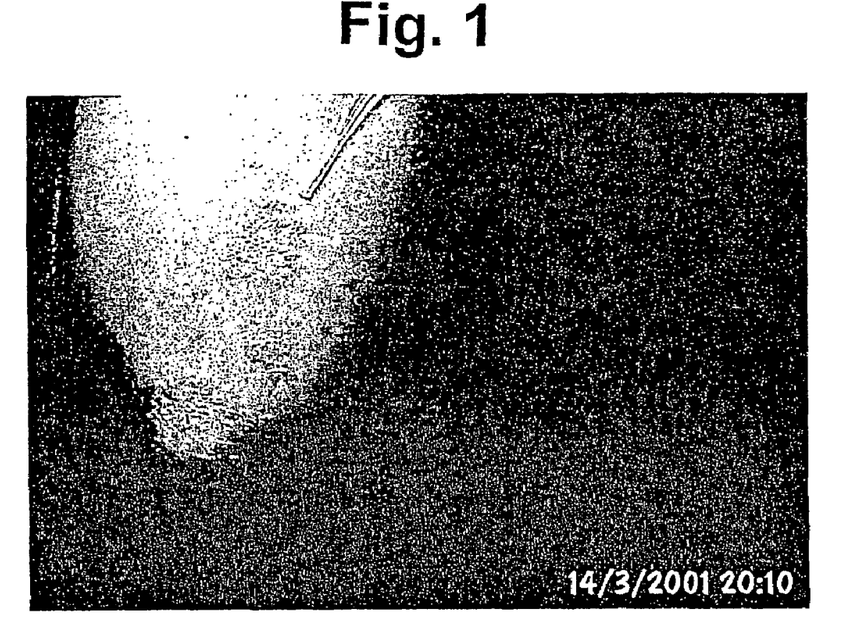
FIG. 1: Day 0, psoriatic plaque on left elbow of a patient prior to treatment.
Figure 2:
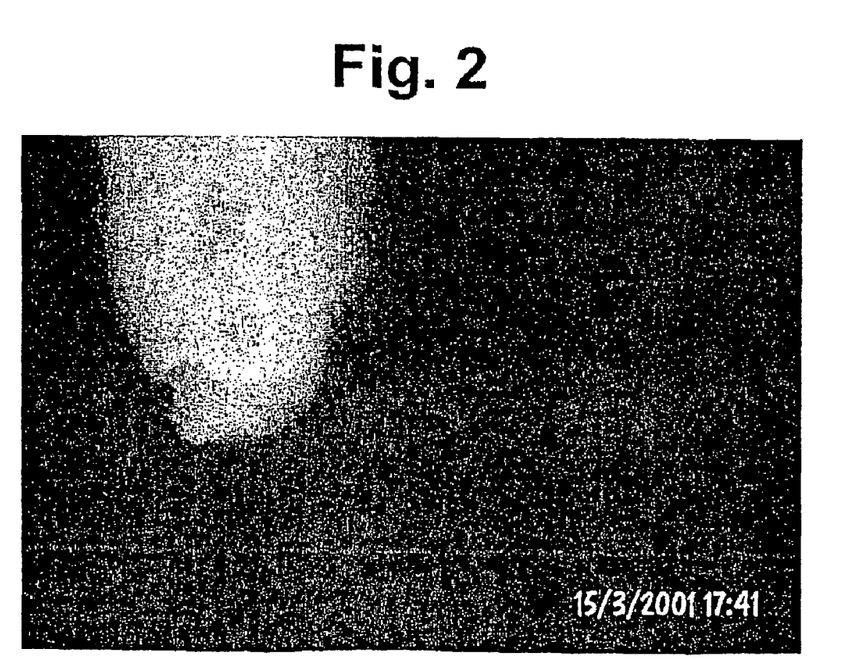
FIG. 2: Day 1, psoriatic plaque on left elbow of patient after 1 day of treatment with ValDerm occlusion bandage after washing and drying.
Figure 3:
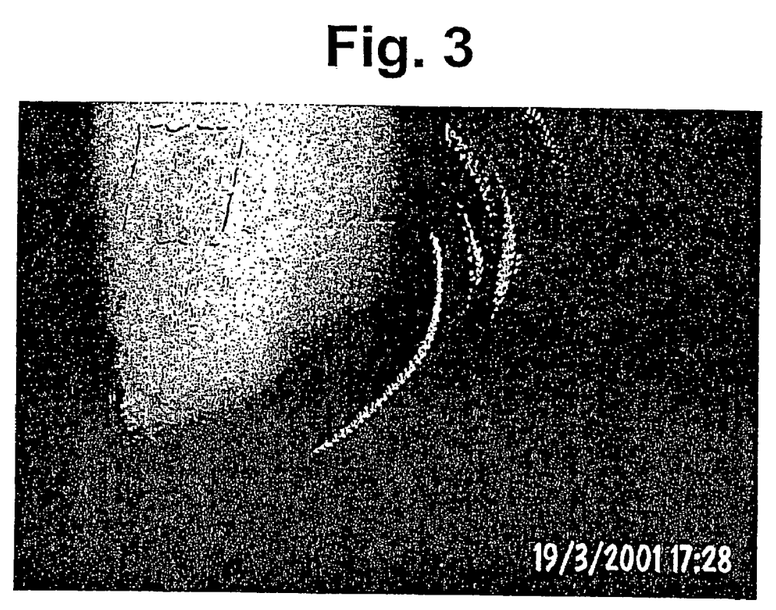
FIG. 3: Day 5, psoriatic plaque on left elbow of patient after 4 days treatment with ValDerm occlusion bandages renewed daily.
Figure 4:
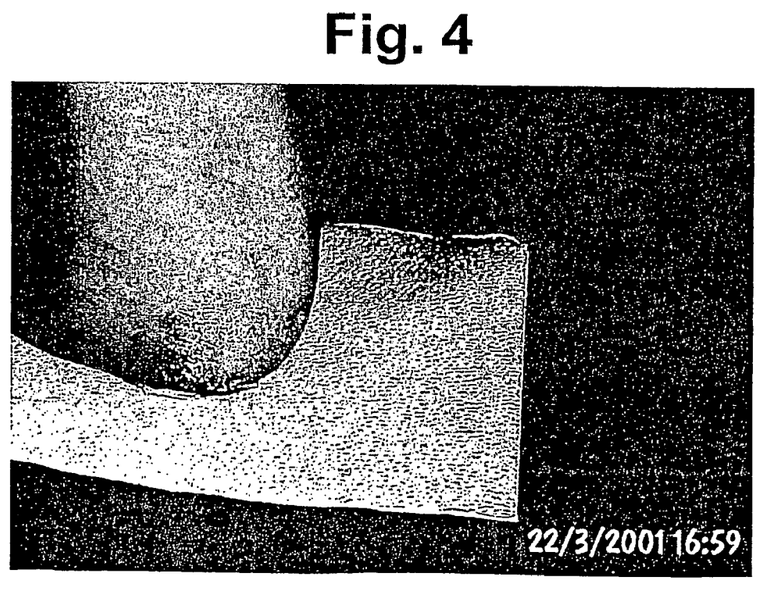
FIG. 4: Day 8, psoriatic plaque on left elbow of patient after 4 days treatment with ValDerm occlusion bandages renewed daily.

There was a clear effect of Valderm after 4 days treatment as shown in FIG. 1 to 4 including smoothening of the treated psoriatic plaques as well as healing with normal looking skin. On day 0 before treatment was initiated, there were clear psoriatic plaques on left elbow (FIG. 1), on day 1 after 1 day of treatment the psoriatic plaques had already become less pronounced (FIG. 2), on day 5 after 4 days of treatment the psoriatic plaques had largely disappeared (FIG. 3) and on day 8 after 4 days of treatment, a further improvement compared to day 5 was observed with increased healing of the psoriatic plaque (FIG. 4).

Around 21 days after cessation of treatment, the psoriatic plaques had reappeared at a size similar to prior to treatment. No rebound phenomena were observed.

The patient was questioned daily about irritation and other side effects of the treatment. The patient did not feel any malaise or irritation at the site of treatment and the patient did not feel any difference in nuisance after treatment with placebo versus ValDerm.

Example 3

Pharmaceutical Solution for Topical Administration Comprising Valrubicin

|  | % (w/w) |
| --- | --- |
| Valrubicin | 1 |
| Castor oil polyoxyl Ph.Eur. | 10 |
| Ethanol | 39 |
| Glycerol anhyd. | 50 |
| Total | 100 |

Example 4

Pharmaceutical Solution for Topical Administration Comprising Valrubicin

|  | % (w/w) |
| --- | --- |
| Valrubicin | 1 |
| Polysorbate 20 | 10 |
| Ethanol | 39 |
| Glycerol anhyd. | 50 |
| Total | 100 |

Example 5

Pharmaceutical Solution for Topical Administration Comprising Valrubicin

|  | % (w/w) |
| --- | --- |
| Valrubicin | 2 |
| Castor oil polyoxyl Ph.Eur. | 5 |
| Polysorbate 20 | 5 |
| Ethanol | 38 |
| Glycerol anhyd. | 50 |
| Total | 100 |

Example 6

Pharmaceutical Gel for Topical Administration Comprising Valrubicin

|  | % (w/w) |
| --- | --- |
| Valrubicin | 1 |
| Polysorbate 20 | 10 |
| Ethanol | 40 |
| Polyethylene glycol 6000 | 49 |
| Total | 100 |

Example 7

Pharmaceutical Solution for Topical Administration Comprising Valrubicin

|  | % (w/w) |
| --- | --- |
| Valrubicin | 1 |
| Castor oil polyoxyl Ph.Eur. | 15 |
| Ethanol | 54 |
| Propylene glycol | 30 |
| Total | 100 |

Example 8

Pharmaceutical Solution for Topical Administration Comprising Valrubicin

|  | % (w/w) |
| --- | --- |
| Valrubicin | 0.5 |
| Castor oil polyoxyl Ph.Eur. | 5 |
| Ethanol | 30 |
| Glycerol anhyd. | 39.5 |
| Propylene glycol | 20 |
| Isopropyl myristate | 5 |
| Total | 100 |

Example 9

Pharmaceutical Composition for Topical Administration Comprising Valrubicin

|  | % (w/w) |
| --- | --- |
| Valrubicin | 1 |
| Castor oil polyoxyl Ph.Eur. | 5 |
| Polysorbate 20 | 5 |
| Ethanol | 35 |
| Glycerol anhyd. | 49 |
| Paraffin oil | 5 |
| Total | 100 |

Example 10

Pharmaceutical Gel for Topical Administration Comprising Valrubicin

| | % (w/w) |
|---|---|
| Valrubicin | 0.7 |
| Castor oil polyoxyl Ph. Eur. | 7 |
| Ethanol | 35 |
| Glycerol anhydrate | 32.3 |
| Polyethylene glycol 6000 | 20 |
| Cetyl alcohol | 5 |
| Total | 100 |

Example 11

A Clinical Trial, Topical Therapy of Psoriasis Vulgaris

A patient having dermal manifestations of psoriasis vulgaris was selected for therapy using the invention. Valrubicin was prepared as a solution (ref ex: 5) at a concentration of 2% (weight/weight) and was applied to the affected skin once daily.

The patient was monitored for improvement in his manifestations of psoriasis. After the skin lesions had subsided, therapy was discontinued.

Example 12

A clinical Trial, Topical Therapy of Psoriasis Vulgaris

A patient having dermal manifestations of psoriasis vulgaris was selected for therapy using the invention. Valrubicin was prepared as a solution (ref ex. 8) at a concentration of 0.5% (weight/weight) and was applied to the affected skin once daily. The patient was monitored for improvement in his manifestations of psoriasis. After the skin lesions had subsided, therapy was discontinued.

Example 13

A clinical Trial, Topical Therapy of Psoriasis Vulgaris

A patient having dermal manifestations of psoriasis vulgaris was selected for therapy using the invention. Valrubicin was prepared as a gel (ref ex. 6) at a concentration of 1% (weight/weight) and was applied to the affected skin once daily. The patient was monitored for improvement in his manifestations of psoriasis. After the skin lesions had subsided, therapy was discontinued.

Example 14

A Clinical Trial, Topical Therapy of Psoriasis Vulgaris

A patient having dermal manifestations of psoriasis vulgaris was selected for therapy using the invention. Valrubicin was prepared as a solution (ref. ex 5) at a concentration of 2.0% (weight/weight) and was applied to the affected skin twice daily. The patient was monitored for improvement in his manifestations of psoriasis. After the skin lesions had subsided, therapy was discontinued.

Example 15

A Clinical Trial, Topical Therapy of Psoriasis Vulgaris

A patient having dermal manifestations of psoriasis vulgaris was selected for therapy using the invention. Valrubicin was prepared as a solution (ref. ex 5) at a concentration of 2.0 (weight/weight) and was applied to the affected skin twice a week. The patient was monitored for improvement in his manifestations of psoriasis. After the skin lesions had subsided, therapy was discontinued.

Example 16

A Clinical Trial, Topical Therapy of Psoriasis Vulgaris

A patient having dermal manifestations of psoriasis vulgaris has selected for therapy using the invention. Valrubicin was prepared as a solution (ref. ex 5) at a concentration of 2.0% (weight/weight) and was applied to the affected skin once a week. The patient was monitored for improvement in his manifestations of psoriasis. After the skin lesions had subsided, therapy was discontinued.

REFERENCES (1) Dantchev D, Slioussartchouk V, Paintrand M, Hayat M, Bourut C, Mathe G. Electron microscopic studies of the heart and light microscopic studies of the skin after treatment of golden hamsters with adriamycin, detorubicin, AD-32, and aclacinomycin. Cancer Treat Rep 1979; 63(5):875-888.

(2) Dantchev D, Slioussartchouk V, Paintrand M, Bourut C, Hayat M, Mathe G. Ultrastructural study of the cardiotoxicity and light-microscopic findings of the skin after treatment of golden hamsters with seven different anthracyclines. Recent-Results Cancer Res 1980; 74:223-249.

(3) Dantchev D, Balercia G, Bourut C, Anjo A, Maral R, Mathe G. Comparative microscopic study of cardiotoxicity and skin toxicity of anthracycline analogs. Biomed Pharmacother 1984; 38(7):322-328.

(4) Expert report. 21.
Ref Type: Generic (5) Onrust S V, Lamb H M. Valrubicin. Drugs Aging 1999; 15(1):69-75.

(6) Sweatman T W, Parker R F, Israel M. Pharmacologic rationale for intravesical N-trifluoroacetyladriamycin-14-valerate (AD 32): a preclinical study. Cancer Chemother Pharmacol 1991; 28(1):1-6.

(7) FDA. Valstar (Valrubicin) Sterile Solution. 2001.

The invention claimed is:

1. A method of treatment of a condition of a body surface, wherein said condition is psoriasis, in an individual in need thereof, comprising topically administering a therapeutically and topically effective amount of valrubicin, or a pharmaceutically acceptable salt thereof, to said individual.

2. The method according to claim 1, wherein the individual is a human being.

3. The method according to claim 1, wherein the body surface is skin.

4. The method according to claim 1, wherein the body surface is a mucosal membrane.

5. The method according to claim 1, wherein the body surface is selected from the group consisting of mouth and genital tract.

6. The method according to claim 1, wherein the body surface is the oral cavity.

7. The method according to claim 1, wherein the treatment is ameliorating treatment.

8. The method according to claim 1, wherein administration is more than once.

9. The method according to claim 1, wherein the method of treatment is repeated at every occurrence and/or reoccurrence of the condition.

10. The method according to claim 1, wherein the method furthermore comprises a second treatment for psoriasis.

11. The method according to claim 10, wherein the second treatment is selected from the group consisting of treatment with sunlight, ultraviolet light B (UVB) or PUVA.

12. The method according to claim 10, wherein the second treatment is administration of a compound selected from the group consisting of steroids, coal tar, calcipotriene, vitamin A, anthralin, salicylic acid, methotrexate, retinoids and cyclosporin.

13. The method according to claim 1 wherein the psoriasis is selected from the group consisting of psoriasis vulgaris, guttate psoriasis, flexural psoriasis, erythrodermic psoriasis, generalized pustular psoriasis, and localized pustular psoriasis.

14. The method according to claim 1 wherein the psoriasis is psoriasis vulgaris.

* * * * *